US00PP26366P2

(12) United States Plant Patent
Kordes

(10) Patent No.: US PP26,366 P2
(45) Date of Patent: Feb. 2, 2016

(54) FLORIBUNDA ROSE PLANT NAMED 'KORFLOCI54'

(50) Latin Name: *Rosa hybrida*
Varietal Denomination: KORfloci54

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 60 days.

(21) Appl. No.: 13/987,162

(22) Filed: Jul. 3, 2013

(51) Int. Cl.
*A01H 5/02* (2006.01)

(52) U.S. Cl.
USPC ..... Plt./147

(58) Field of Classification Search
USPC ..... Plt./146, 147
CPC ..... A01H 5/0222
See application file for complete search history.

(56) References Cited

PUBLICATIONS

Chamblee's Rose Nursery, retrieved from internet Nov. 5, 2014.*
Plant License Agreement which contains reference to the instant variety, 2012.

* cited by examiner

*Primary Examiner* — Keith O. Robinson

(57) ABSTRACT

A new and distinct variety of rose with long lasting, novel salmon orange flowers, and attractive foliage with excellent disease resistance. It exhibits compact growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida*.

Variety denomination: The denomination of the new variety is 'KORfloci54'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2002. The crossing was between an 'un-named seedling', the seed parent, and another 'un-named seedling', the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated by budding for further evaluation. This new and distinctive rose variety is named 'KORfloci54'.

SUMMARY OF THE INVENTION

The new rose plant may be distinguished from its seed parent, an 'un-named seedling', by the following combination of characteristics:

1. 'KORfloci54' has salmon orange flowers, whereas the 'un-named seedling' has red flowers.
2. 'KORfloci54' has approximately 60 petals, whereas the 'un-named seedling' has 25-30 petals.

The new rose plant maybe distinguished from its pollen parent, an 'un-named seedling', by the following combination of characteristics:

1. 'KORfloci54' has salmon orange flowers, whereas the 'un-named seedling' has cream white flowers.
2. 'KORfloci54' has a compact growth habit, whereas the 'un-named seedling' has an upright growth habit.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORfloci54' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfloci54' was selected in May 2003 from the seedling beds to be asexually propagated for further evaluation. The first asexual propagation of 'KORfloci54' was done by budding in July 2003 at the inventor's nursery in Offenseth-Sparrieshoop, Germany.

These initial and other subsequent propagations conducted in controlled environments demonstrate that 'KORfloci54' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and sterns of 'KORfloci 54' taken from a 1-year-old plant growing in a nursery in Jackson County, Oreg.

DETAILED BOTANICAL DESCRIPTION

The following is a description of 'KORfloci54', as observed growing in June 2013 in a nursery in Jackson County, Oreg. on plants of 1 year of age. Color references are made using The Royal Horticultural Society (London, England) Colour Chart, 2001 except where common terms of color are used.

For a comparison, several physical characteristics of the rose variety 'KORliolow', a rose variety from the same inventor described and illustrated in U.S. Plant Pat. No. 21,472 and issued on Nov. 16, 2010 are compared to 'KORfloci54' in Chart 1.

CHART 1

| Characteristic | 'KORfloci54' | 'KORliolow' |
|---|---|---|
| Plant height | 70 cm | 100-110 cm |
| Plant habit | Compact; bushy | Upright to bushy |
| Foliage | 7 leaflets per leaf | 3-5 leaflets per leaf |

Parents:

*Seed parent*.—An 'un-named seedling'.

*Pollen parent*.—An 'un-named seedling'.

Classification:

*Botanical classification*.—*Rosa hybrida* 'KORfloci54'.

*Commercial classification*.—Floribunda rose.

FLOWER AND FLOWER BUD

Blooming habit: Recurrent. Prolific.

Flower bud:

*Size*.—Upon opening, 30 mm in length from base of receptacle to distal end of bud and 20-25 mm diameter at its widest point.

*Bud form*.—Short. Globular.

*Bud color*.—As sepals first unfold, bud color is Red Group 43D. When ¼ open, the upper surface of petals is Red Group 43C, and the lower surface is Red Group 52D.

*Sepals*.—Color: Upper surface Yellow-Green Group 146C. Lower surface Yellow-Green Group 146B. Intonations of Greyed-Purple Group 183C on upper and lower sides and along margin. Size: Average 25-30 mm (l)×10-12 mm (w). Shape: Weak foliaceous appendages on 2-3 of the five sepals. Apex: Apiculate. Base: Flat at union with receptacle. Quantity: Five. Diameter of the calyx: Variable. 15 to 23 mm. Surface texture: Upper side: Lightly pubescent. Lower surface: Lightly pubescent with stipitate glands. Margins: Pubescent with stipitate glands.

Flower bloom:

*Fragrance*.—Very light.

*Duration*.—On the plant 4-6 days. Senesced petals drop away cleanly.

*Size*.—Large for a floribunda rose. When open, the average flower diameter is 70 mm and the average flower height is 30 mm.

*Form*.—Shape of flower when viewed from the side: Upon opening, upper part: Flat. Upon opening, lower part: Concave. Open flower, upper part: Flat. Open flower, lower part: Flat.

Color:

*Upon opening, petals*.—Outermost petals: Outer Side: Red Group 48D. Inner Side: Red Group 52B. Innermost petals: Outer Side: Red Group 52C. Inner Side: Red Group 43B.

*Upon opening, basal petal spots*.—Basal petal spot, outermost petals: Outer Side: Green-Yellow Group 1C. Inner Side: Green-Yellow Group 1B. Basal petal spot, innermost petals: Outer Side: Green-Yellow Group 1C. Inner Side: Green-Yellow Group 1A.

*After opening, petals*.—Outermost petals: Outer Side: Red Group 55C. Inner Side: Red Group 54B. Innermost petals: Outer Side: Red Group 54C. Inner Side: Red Group 50B.

*After opening, basal petal spots*.—Basal petal spot, outermost petals: Outer Side: White Group 155B. Inner Side: White Group 155B. Basal petal spot, innermost petals: Outer Side: Green-White Group 155C. Inner Side: Yellow-Green Group 154D.

General tonality: On open flower Red Group 43C and Red Group 43D. No change in the general tonality at the end of the $4^{th}$ day. Afterwards, general tonality is Red Group 54D.

Petals:

*Petal count*.—Very Double. Approximately 60 petals under normal conditions.

*Petal reflex*.—Petals reflex somewhat. Petal reflex occurs one by one beginning with outermost petals.

*Petal margin*.—Entire.

*Petal shape*.—Variable with outer petals obovate and inner petals elliptical. Apex: Obtuse. Base: Cuneate.

*Petal size*.—15-35 mm (l)×10-25 mm (w).

*Size of the basal spot*.—2.5-4.5 mm (l)×2.5-4.5 mm (w).

*Thickness*.—Thin.

*Petal arrangement*.—Quartered cup.

*Texture*.—Outer Side: Smooth. Inner Side: Smooth.

Petaloids:

*Petaloid count*.—Average of 30-35 per flower.

*Petaloid size*.—10-20 mm (l)×5-15 mm (w).

*Petaloid color*.—Inner side: Red Group 54C. Outer side: Red Group 50B.

*Petaloid texture*.—Outer Side: Smooth. Inner Side: Smooth.

*Margins*.—Entire to indented.

*Petaloid shape*.—Highly irregular. Apex: Acute to obtuse. Base: Typically attenuate.

Reproductive organs:

*Pistils*.—Few. Approximately 18 present. Stigmas: Location: Slightly superior in position to anthers. Color: Greyed-Orange Group 163D. Diameter: 1 mm. Styles: Length: About 9 mm long. Color: Greyed-Yellow Group 160D. Intonations of Greyed-Red Group 178A.

*Stamens*.—Approximately 50 on average and regularly arranged. Anthers: Size: Average 4-6 mm (l)×1 mm (w). Pollen: Generally present. Color: Greyed-Yellow Group 162B. Filaments: Color: Yellow-Orange Group 15B. Length: 5-6 mm.

Receptacle:

*Color*.—Yellow-Green Group 146C.

*Shape*.—Urn-shaped.

*Texture*.—Smooth.

*Size*.—15 mm (h)×12-15 mm (w).

Pedicel:

*Surface*.—With abundant stipitate glands.

*Length*.—10-35 mm average length.

*Diameter*.—2-3 mm average diameter.

*Color*.—Yellow-Green Group 146D. Intonations of Greyed-Orange Group 146B. Anthocyanin covering 60-90% of pedicel.

*Strength*.—Somewhat strong.

*Texture*.—Smooth.

Peduncle:

*Surface*.—No stipitate glands or prickles present.

*Length*.—50-80 mm average length.

*Diameter*.—3-5 mm average diameter.

*Color*.—Yellow-Green Group 146D. Intonations of Greyed-Orange Group 146B.

*Strength*.—Somewhat strong.

*Texture*.—Smooth.

*Borne*.—Multiple flower buds per stem, generally 1 to 3.

THE PLANT

Growth: Vigorous growth.

Plant habit: Compact. Bushy. When grown as a nursery plant, the average plant height is 70 cm and the average plant width is 60 cm.

Stems:

*Average length*.—30-35 cm.

*Average diameter*.—3-6 mm.

*Stem color*.—Youngwood: Yellow-Green Group 146C. Older wood: Yellow-Green Group 146B.

*Anthocyanin*.—Greyed-Orange Group 176B generally present on new growth.

*Stem surface texture*.—Young wood: Smooth. Older wood: Smooth.

*Flowering laterals*.—Present, typically 1 to 3 flowering laterals arising from each cane, with 3 to 5 flowers per lateral.

Prickles: Present.

*Incidence*.—Average of 8 per each 10 cm of stem.

*Size*.—Average length: 8 mm.

*Color*.—Immature prickles: Greyed-Red Group 180A. Mature prickles: Greyed-Purple Group 183B.

*Anthocyanin*.—Completely covers all prickles. Immature prickles: Greyed-Red Group 180A. Mature prickles: Greyed-Purple Group 183B.

*Shape*.—Concave.

Leaves: Normally 7 leaflets on normal leaves in middle of the stem.

*Venation pattern*.—Pyramidal net pattern.

*Leaf size*.—120 mm (l)×90-100 mm (w).

*Abundance*.—Very.

Leaflets:

*Size*.—Average size of the terminal leaflet is 45-50 mm (l)×30-35 mm (w).

*Shape*.—Ovate. Base: Obtuse. Apex: Acute.

*Margins*.—Serrated.

*Surface*.—Semi-glossy.

*Thickness*.—Thick.

*Texture*.—Upper side of leaflet: Smooth. Under side of leaflet: Smooth.

*Color, mature foliage*.—Upper Leaflet Surface: Green Group 137A. Lower Leaflet Surface: Yellow-Green Group 147C.

*Color, juvenile foliage*.—Upper Leaflet Surface: Green Group 137C. Lower Leaflet Surface: Yellow-Green Group 147C.

*Anthocyanin intonation*.—Greyed-Red Group 178A. Location: Lower and upper sides of immature foliage.

*Arrangement*.—Odd pinnate.

*Venation*.—Reticulate.

Stipules:

*Size*.—28 mm (l)×12 mm (w).

*Stipule color*.—Yellow-Green Group 147B.

*Anthocyanin*.—Greyed-Red Group 182B. Slight intonations along center rib of upper side.

*Stipitate glands*.—Located on margins and rarely on underside.

*Shape*.—Apex: Apiculate. Base: Winged.

Petiole:

*Length*.—Average 10 mm.

*Diameter*.—Average 1.5 mm.

*Petiole color*.—Yellow-Green Group 146B. Underneath: Yellow-Green Group 146C.

*Prickles*.—Present.

*Stipitate glands*.—Abundant on upper side and along margin.

*Texture*.—Smooth.

Petiole rachis:

*Length*.—Average 15-20 mm.

*Diameter*.—Average 2mm.

*Color*.—Yellow-Green Group 146B. Anthocyanin present on upper side at leaflet attachment: Greyed-Purple Group 184B.

*Margins*.—With stipitate glands.

*Prickles*.—Prickles underneath at point of leaflet attachment.

*Texture*.—Smooth.

Hips/seed formation: None observed.

Winter hardiness: To date, the variety has been grown successfully in Zone 5B.

Disease resistance: Excellent resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

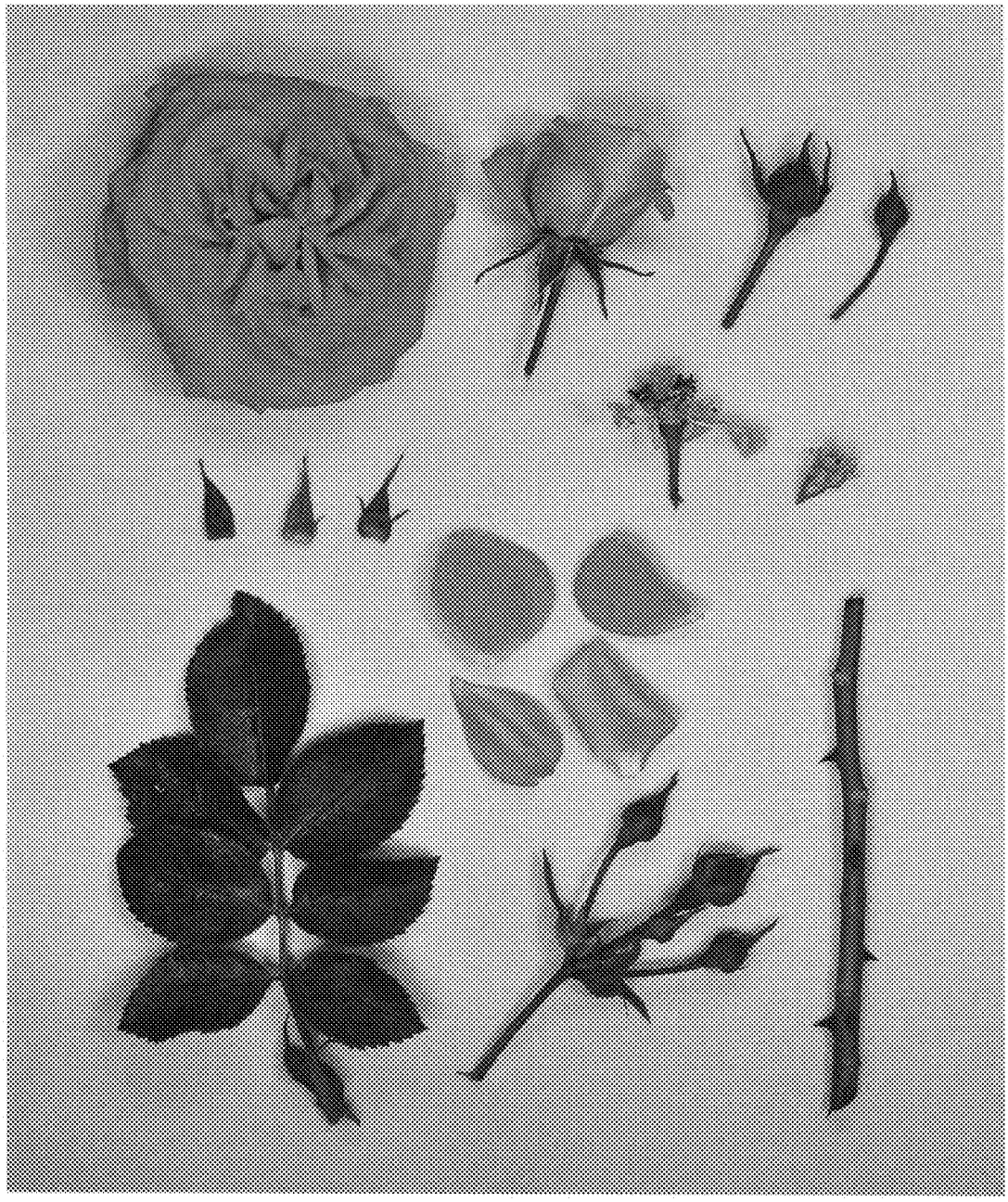

* * * * *